United States Patent [19]
Joo et al.

[11] Patent Number: 6,071,933
[45] Date of Patent: Jun. 6, 2000

[54] HOMOGENEOUS REMIFENTANIL-PROPOFOL BLEND FOR PATIENT CONTROLLED ANESTHESIA AND PROCESS FOR ITS USE

[75] Inventors: Hwan Joo, Toronto; William Perks, Etobicoke; Hanna Samulska, Toronto, all of Canada

[73] Assignee: Diversified Medical Innovations, Inc., Ontario, Canada

[21] Appl. No.: 09/452,860

[22] Filed: Dec. 3, 1999

[51] Int. Cl.[7] .......................... A61K 31/445; A61K 31/05
[52] U.S. Cl. .............................................. 514/329; 514/731
[58] Field of Search ....................... 514/329, 731

[56] References Cited

U.S. PATENT DOCUMENTS

| | | | |
|---|---|---|---|
| 5,637,625 | 6/1997 | Haynes | 514/731 |
| 5,866,591 | 2/1999 | Gatlin et al. | 514/329 |
| 5,908,869 | 6/1999 | Jones et al. | 514/731 |

*Primary Examiner*—Raymond Henley, III
*Attorney, Agent, or Firm*—McHale & Slavin

[57] ABSTRACT

The present invention utilizes a homogeneous mixture of Propofol (2,6-diisopropylphenol) and Remifentanil (N-Phenyl-N-(4-piperidinyl) amides), designed to deliver a constant proportion of drugs to the patient, specifically designed to provide enhanced results when administered via a PCA modality. The Remifentanil/Propofol homogeneous mixture (REMIPRO) is supplied in a dosage range of 1,000 parts Propofol to 10 parts Remifentanil (1,000 microgram Propofol: 10 microgram Remifentanil) to 20,000 parts Propofol to 10 parts Remifentanil (20,000 microgram Propofol: 10 ug Remifentanil). Induction of anesthesia via REMIPRO provides increased patient and physician satisfaction, increased safety, and decreased overall cost as the patient will be more alert after the procedure and will leave the hospital faster.

12 Claims, No Drawings

HOMOGENEOUS REMIFENTANIL-PROPOFOL BLEND FOR PATIENT CONTROLLED ANESTHESIA AND PROCESS FOR ITS USE

FIELD OF THE INVENTION

This invention relates to intravenously instilled anesthesia; particularly to a homogeneously blended product for delivering a constant proportion of Remifentanil (N-Phenyl-N-(4-piperidinyl) amides) and Propofol (2,6-diisopropylphenol), and most particularly to instillation of the homogeneously blended product by a patient controlled anesthesia (PCA) modality.

BACKGROUND OF THE INVENTION

Anesthesia is generally administered by physicians or on the order of physicians. Typically, the drugs of choice consist of opioids, benzodiazapines, Propofol and muscle relaxants. These drugs are administered in a variety of ways; for example a particularly determined amount of one or more drugs may be administered parenterally in a single bolus designed to induce a loss of consciousness. Various combinations of drugs are administered so as to achieve a state of muscle relaxation, hypnosis and analgesia. Alternatively, various of these medications may be administered for monitored anesthesia care (MAC), by intermittent boluses or a constant infusion pump. They may be under computer control, patient control, or a combination, (target controlled PCA) wherein a targeted level of anesthesia is preset in the automated control mechanism, with a provision for on-demand patient dosing up to a secondarily determined level. Among the opioids, Alfentanil and Remifentanil are well-known medications, useful as primary analgesics, or in combination with additional medicaments. Monitored anesthesia care (MAC) is possible with a combination of neuroleptic, sedative and analgesic medications. However, physician administered MAC may be associated with under-dosing and overdosing, often during the same procedure, on the same patient. This may lead to patient discomfort or prolonged recovery depending on the situation.

The choice of medications is predicated on the speed of onset and offset with which they are metabolized. Administration of long lasting opioids often lead to delays in recovery of mental and respiratory function. Constant vigilance must be maintained during recovery from MAC since respiratory depression and/or cessation of breathing is possible during the recovery period. Alternatively, if a medication is chosen with too short a half-life, and the physician attempts to maintain a very low threshold level, it is possible that drug levels will fall too quickly and the patient will experience pain or untoward effects due to lack of an anesthetic level being maintained. To further compound the matter, the most efficacious mode of administration needs to be chosen. Whether via bolus administration, constant infusion, targeted PCA, or PCA per se, the comfort, safety, and recovery of the patient must be protected and maintained.

Alfentanil, an opioid which has a relatively long half-life, has been used alone and in conjunction with other sedatives, for example hypnotic drugs. Dell et al. utilized an admixture of Alfentanil and Propofol in a PCA modality for patient-controlled sedation during transvaginal oocyte retrieval. Propofol, a powerful sedative having a therapeutic half-life on the order of 3–5 minutes, is often used as an adjunct medication, and is infused in conjunction with other sedatives. The admixture of Alfentanil and Propofol raises the fear of respiratory depression. Because Alfentanil has an elimination half-time of 70–98 minutes and context-sensitive half-time of 12–60 minutes depending on the duration of infusion, Alfentanil may be too long acting for short painful procedures, which are not associated with pain after the procedure. It may lead to prolonged recovery in the PACU or in the worst cases, respiratory arrest when the stimulus is no longer present while the effects of the drugs are still active.

Remifentanil, an ultrashort acting opioid (in the morphine family) with a half-life of only 3 minutes, is marketed under the trade name ULTIVA (TM). Remifentanil has been used for sedation with mixed success. It has been given as an infusion, a bolus medication or a target controlled PCA, where a computer controls the rate of infusion, maintaining a baseline level of anaesthesia while allowing for additional controlled dosing based upon patient demand or lack of demand. Inclusion of Remifentanil in an admixture for a total PCA modality would be counter-intuitive to the skilled practitioner since its short half-life may lead to inadequate pain control. Remifentanil has been used in conjunction with Midazolam (a sedative similar to Valium) using a conventional infusion pump, with a greater degree of success, however, there is some reluctance on the part of physicians due to the constant vigilance required by the physician using a constant dose infusion regimen.

Remifentanil may be a better drug for MAC and PCA due to its rapid onset and rapid offset, however these characteristics render it difficult to maintain overall control and patient satisfaction. Remifentanil has a context-sensitive half-time of 3 minutes, no matter the duration of infusion. Sa et al in 1999 investigated the use of Remifentanil for lithotripsy given as infusion only, infusion+bolus and bolus Remifentanil only. They reported that patient satisfaction and pain control was best in infusion+bolus, and bolus groups but the incidence of transient apneas were also the most common in the group where bolus medications were given. The transient apneas may have been due to the fact that the physicians gave relatively large boluses of Remifentanil and therefore may have transiently overdosed the patients. All study patients also received a bolus dose of Midazolam and an infusion of propofol, which may have affected patient sedation and complication.

It is the premise of the instant inventors that patients are the best judges of adequate pain control and sedation. Although Remifentanil, given as a PCA in small boluses should lead to optimal patient satisfaction and minimal adverse effects, Remifentanil itself will not treat patient anxiety and sedative medication is required for adequate MAC. (Gold 1997). Past attempts at administering combinations of medications have had limited success because they focused on controlling separate and distinct infusions of various of the combinations medicaments. Recognizing this, the present inventors have created a homogeneous blend of Remifentanil and Propofol which provides an optimal sedative effect when administered via a PCA modality.

If a combination of ultra-short acting analgesics and sedatives can be provided which provide an effective level of anesthesia via a PCA modality, prolonged sedation can be avoided in procedures which have minimal or no postoperative pain. By having the patient awake and alert at the end of the procedure, time to discharge from the postoperative care unit (PACU) will be shortened, thereby saving health care resources while minimizing postoperative morbidity.

DESCRIPTION OF THE PRIOR ART

Karthick Vishwanathan et al, HPLC Determination of a Propofol and Remifentanil Mixture, outlines two separate High Performance Liquid Chromatography procedures for the assay of a remifentanil-propofol mixture. The separation and quantitation of remifentanil were achieved on an ethylsilane column at ambient temperature (23° C.) using a mobile phase of 62:38 v/v 0.01 M phosphate buffer pH 2.5-acetonitrile at a flow rate of 2 mL/min with detection at 210 nm. A methylsilane column at 23° C. using the same mobile phase at a flow rate of 1.0 mL/min with detection at 210 nm was used for propofol. The methods showed linearity for remifentanil and propofol in the 1.0–45 and 15–75 microgram/ml ranges, respectively. Accuracy and precision were in 0.08–2.3% and 0.2–1.2% ranges, respectively, for both drugs. The limits of detection for Remifentanil and Propofol were 200 and 250 ng/mL, respectively, based on a signal to noise ratio of 3 and a 10 microgram injection.

Mann et al. describes intraoperative remifentanil patient controlled analgesia using PCA Remifentanil with a 5 microgram bolus and a 3 minute lockout. They concluded that at this dose, some patients could not tolerate the pain for that procedure. This seems to have been an inadequate dose. Dell and Cloote disclosed patient-controlled sedation during transvaginal oocyte retrieval using a mixture of propofol and Alfentanil. This reference describes a mixture of Propofol and Alfentanil, no mention is made of Remifentanil. Alfentanil is too long acting for effective use in most procedures where PCA is used.

Chin et al discloses the use of patient-controlled analgesia in extracorporeal shockwave lithotripsy. Herrick et al describes patient-controlled sedation using Propofol during interventional neuroradiologic procedures. They concluded that PCA Propofol approaches the limit of safety. Heiman et al. describes Patient-controlled anesthesia for colonoscopy using Propofol. They used Propofol PCA in one group and Propofol mixed with Alfentanil in the other group. Their conclusion was that Propofol-Alfentanil mixture was better. Again Alfentanil may last too long when compared to Propofol. The offset time of Alfentanil is much longer than Propofol. The mixture of Remifentanil and Propofol is ideal due to similar onset and offset of these drugs.

Johnson et al discloses the use of Remifentanil in conjunction with Propofol for awake craniotomy. The drugs were actually given separately and not as a single homogeneous admixture as instantly disclosed.

G. Schoiz et al, teaches the pharmacokinetics of propofol in combination with remifentanil. This is an article relating to the combined use in the body, using separate infusion pumps. It does not describe a mixed drug given in fixed combination.

SUMMARY OF THE INVENTION

The present invention utilizes a homogeneous mixture of Propofol and Remifentanil, designed to deliver a constant proportion of drugs to the patient, specifically designed to provide enhanced results when administered via a PCA modality. The Remifentanil/Propofol homogeneous mixture (REMIPRO)is supplied in a dosage range of 1,000 parts Propofol to 10 parts Remifentanil (1,000 microgramPropofol: 10 microgram Remifentanil) to 20,000 parts Propofol to 10 parts Remifentanil (20,000 microgram Propofol: 10 microgram Remifentanil).

REMIPRO is an ideal drug due to improved patient sedation and decreased incidence of nausea, itchiness and respiratory depression when compared to Remifentanil. REMIPRO's advantage over Propofol is that the patient will have pain relief without becoming unconscious. The use of REMIPRO provides increased patient satisfaction and increased physician satisfaction as patient co-operation is improved. Patient safety is increased as in some procedures, the physician giving the sedation is also performing the procedure. Physicians may, therefore, not be observing their patients. Patients will be more alert after the procedure and will leave the hospital faster, decreasing overall healthcare cost.

The instant invention teaches the use of REMIPRO with a conventional PCA machine Grasby 3300). REMIPRO can be used as bolus on demand and bolus on demand with background infusion. The advantage of a conventional PCA is that it may be safer, more applicable for sedation and obviates the need for expensive, computer processed target controlled analgesia.

Accordingly, it is an objective of the instant invention to teach a homogeneous admixture of Remifentanil and Propofol designed to deliver a constant proportion of drugs to the patient.

It is a further objective of the instant invention to teach a combination of Remifentanil and Propofol specifically designed to provide enhanced results when administered via a PCA modality.

Other objects and advantages of this invention will become apparent from the following description taken in conjunction with the accompanying drawings wherein are set forth, by way of illustration and example, certain embodiments of this invention.

DETAILED DESCRIPTION OF THE INVENTION

The method of practicing the instant invention is illustrated by way of a particular embodiment as set forth in the following example.

EXAMPLE 1

Various doses of Propofol with Remifentanil can be combined for use during procedures requiring intense analgesia and sedation such as lithotripsy and ophthalmologic procedures. The combinations of medicaments can be provided in the following admixtures:

A) 0 cc of 10 mg/cc Propofol with 40 cc of 10 microgram Remifentanil/1 cc of normal saline for a final concentration of 10 microgram/cc of pure Remifentanil.

B) 4 cc of 10 mg/cc of Propofol and 36 cc of 11.11 microgram/cc Remifentanil for a final solution of 1 mg Propofol and 10 microgram of Remifentanil/cc of solution.

C) 10 ccof 10 mg/cc of propofol with 30 cc of 13.3 microgram Remifentanil/1 cc of normal saline for a final concentration of 2.5 mg Propofol and 10 microgram of Remifentanil/cc of solution.

D) 20 cc of 10 mg/cc of Propofol with 20 cc of 20 microgram Remifentanil/1 cc of normal saline for a final concentration of 5.0 mg Propofol and 10 microgram of Remifentanil/cc of solution.

E) 40 cc of 10 mg/cc of Propofol with 1 cc of 410 microgram Remifentanil/1 cc of normal saline for a final concentration of 9.76 mg Propofol and 10 microgram Remifentanil/cc of solution.

F) 40 cc of 10 mg/cc of Propofol with 200 microgram of powdered Remifentanil for a final solution of 10 mg Propofol and 5 microgram of Remifentanil/cc of solution.

In a most preferred embodiment, the mixture utilized contained 5000 microgram Propofol to 10 microgram of Remifentanil. Illustrative of solutions useful in the instant invention are standard Propofol emulsion formulations, for example EDTA propofol formulation, e.g. as shown in U.S. Pat. No. 5,908,869, 5,731,356; N-methylpyrrolidone-propylene glycol, as shown in U.S. Pat. No. 5,962,536; and Propofol minidroplets, as illustrated in U.S. Pat. No. 5,637,625.

Lithotripsy is a noninvasive procedure used to crush renal stones. It causes significant pain and discomfort during the procedure. Monitored anaesthesia care for lithotripsy has traditionally been performed with the anesthesiologist giving analgesics and anxiolytics to the patients. However, this method may be associated with suboptimal analgesics or oversedation.

This experiment studies the effects of patient controlled anesthesia (PCA) using a two drug regimen. Patients will be permitted to control the rate of administration of their anesthetic by pressing on a button attached to a computer controlled syringe pump filled with medications to treat pain and anxiety. Once the PCA button is pressed a small dose of medication is delivered intravenously.

The patients are divided into two groups:

One group receives an initial bolus of Midazolam followed by a Remifentanil PCA.

The second group receives an initial bolus of Midazolam followed by a combined Propofol-Remifentanil PCA.

The parameters recorded are:

1) Patient characteristics such as age, gender, weight, height, etc.;
2) Hemodynamic results including heart rate, blood pressure, respiratory rate and oxygen saturation, measured at every minute;
3) Fluoroscopy time as a measure of surgical conditions. (Longer fluoroscopy time may be required if the patient moves during the procedure);
4) Ability to attain targeted lithotripsy shock in kV;
5) Number and maximal shock intensity;
6) Anesthetic time-defined as time from first to last dose of medication administered in the lithotripsy unit;
7) Number of PCA doses requested by the patient, number of PCA doses delivered and the total dose of PCA medication;
8) Total dose of Midazolam delivered;
9) Incidence of failure of anaesthetic method;
10) Sedation level as assessed by the modified Aldrete score immediately after the end of lithotripsy, upon arrival to the PACU and 10 minutes after arrival; (Patients With an Aldrete score >9 are considered PACU by-passable, however, all patients are admitted to the PACU after the procedure)
11) Time until patient fit for discharge and actual discharge time from the PACU;
12) Intraoperative nausea and vomiting and PONV;
13) Postoperative need for intravenous opioids;
14) Post operative pain (assessed by a patient questionnaire to determine patient recall of pain), maximal pain, and whether they had pruritus;
15) Patient satisfaction with their mode of anesthetic (poor, good, very good, and excellent);
16) Whether the patients will choose the same method of anaesthetic in the future.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification.

What is claimed is:

1. An improved method for providing anesthesia to a mammal comprising:

forming a homogeneous admixture containing an effective amount of methyl[4-(methoxycarbonyl)-4-[(1-oxopropyl) phenylamino]-1-piperidine]-prop anoate, monohydrochloride) and an effective amount of 2,6-diisopropylphenol and pharmaceutically acceptable isomers and acid addition salts thereof in a pharmacologically suitable carrier; and administering said admixture parenterally to said mammal in an amount effective to sedate and control pain while simultaneously maintaining the mammal in a semi-conscious state.

2. The method in accordance with claim 1, wherein said homogeneous admixture includes at least about 1,000–20,000 parts 2,6-diisopropylphenol to 10 parts methyl[4-(methoxycarbonyl)-4-[(1-oxopropyl)phenylamino]-1-piperidine]-propanoate,monohydrochloride).

3. The method in accordance with claim 1, wherein said homogeneous admixture includes at least about 2,500–10,000 parts 2,6-diisopropylphenol to 10 parts methyl[4-(methoxycarbonyl)-4-[(1-oxopropyl)phenylamino]-1-piperidine]-prop anoate,monohydrochloride).

4. The method in accordance with claim 1, wherein said step of administering includes use of a PCA modality.

5. The method in accordance with claim 1, wherein said step of administering includes use of intravenous bolus.

6. The method in accordance with claim 1, wherein said step of administering includes use of intravenous continuous infusion.

7. The method in accordance with claim 1, wherein said step of administering includes use of patient controlled IV bolus.

8. The method in accordance with claim 1, wherein said step of administering includes use of patient controlled continuous IV infusion.

9. The method in accordance with claim 1, wherein said methyl[4-(methoxycarbonyl)-4-[(1-oxopropyl) phenylamino]-1-piperidine]-prop anoate, monohydrochloride) is administered at concentrations in the range of at least about 0.001 mcg/mL total volume to 10 mg/mL total volume.

10. The method in accordance with claim 1, wherein said 2,6-diisopropylphenol is administered at concentrations in the range of at least about 0.001 mg/mL total volume to 100 mg/mL total volume.

11. The method in accordance with claim 6, wherein said admixture is administered by continuous infusion at a rate of from about 0.1 ml/hr to 999 ml/hr.

12. The method in accordance with claim 5, wherein said admixture is administered as a bolus having a volume within the range of about 0.1 ml to 100 ml.

* * * * *